United States Patent [19]

Willms et al.

[11] Patent Number: 4,963,180
[45] Date of Patent: Oct. 16, 1990

[54] HETEROCYCLIC-SUBSTITUTED PHENYLSULFAMATES, AND THEIR USE AS HERBICIDES AND PLANT GROWTH REGULATORS

[75] Inventors: Lothar Willms, 0, Hillscheid; Heinz Kehne, Hofheim am Taunus; Klaus Bauer, Hanau; Hermann Bieringer, Eppstein, all of Fed. Rep. of Germany

[73] Assignee: Hoechst Aktiengesellschaft, Frankfurt am Main, Fed. Rep. of Germany

[21] Appl. No.: 228,000

[22] Filed: Aug. 3, 1988

[30] Foreign Application Priority Data

Aug. 5, 1987 [DE] Fed. Rep. of Germany ....... 3725939
Feb. 27, 1988 [DE] Fed. Rep. of Germany ....... 3806323

[51] Int. Cl.$^5$ .................. A01N 43/54; C07D 239/69; C07D 239/42; C07D 239/50
[52] U.S. Cl. ........................................ 71/92; 544/321; 544/323; 544/332
[58] Field of Search .................... 71/92; 544/321, 323, 544/332

[56] References Cited

U.S. PATENT DOCUMENTS 4,191,553  3/1980  Reap ......................... 71/92
4,534,790  8/1985  Wolf ........................ 544/207
4,678,500  7/1987  Hay ......................... 544/208

FOREIGN PATENT DOCUMENTS 0004163  9/1979  European Pat. Off. .
0165572  12/1985  European Pat. Off. .

Primary Examiner—John M. Ford
Attorney, Agent, or Firm—Curtis, Morris & Safford

[57] ABSTRACT

Compounds of the formula I or their salts

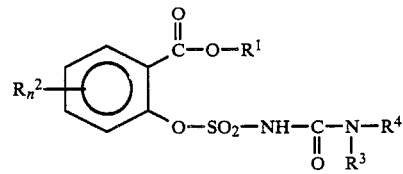

wherein
$R^1$ denotes substituted alkyl; (subst.) alkenyl; (subst.) alkynyl; $R^2$ denotes halogen; nitro; (subst.) alkyl or (subst.) alkoxy; $R^3$ denotes hydrogen; alkyl; alkenyl or alkynyl; $R^4$ denotes a heterocyclic radical or the formulae

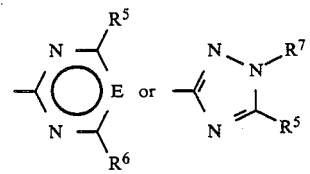

where E is CH or N; and n denotes 0, 1, 2 or 3, possess excellent herbicidal and plant growth-regulating properties.

16 Claims, No Drawings

HETEROCYCLIC-SUBSTITUTED PHENYLSULFAMATES, AND THEIR USE AS HERBICIDES AND PLANT GROWTH REGULATORS

It has been disclosed that heterocyclic-substituted phenoxysulfonylureas exhibit herbicidal and plant growth-regulating properties (cf. EP-A No. 4,163, EP-A No. 165,572).

However, they have disadvantages in their use, such as, for example, high persistence or inadequate selectivity.

It has now been found that heterocyclic-substituted phenylsulfamates which contain specific alkoxycarbonyl groups in the phenyl ester moiety are particularly suitable as herbicides and plant growth-regulators.

The invention therefore relates to compounds of the formula (I) or their salts

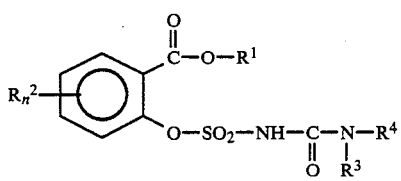

wherein
$R^1$ denotes $(C_1-C_8)$-alkyl which is monosubstituted or polysubstituted by halogen or monosubstituted or di-substituted by $(C_1-C_4)$-alkoxy; $(C_2-C_8)$-alkenyl and $(C_2-C_8)$-alkynyl, both of which are unsubstituted or monosubstituted or polysubstituted by halogen or monosubstituted or disubstituted by $(C_1-C_4)$-alkoxy,
$R^2$ denotes, independently of the other $R^2$s, halogen; nitro; $(C_1-C_4)$-alkyl or $(C_1-C_4)$-alkoxy, both of which are unsubstituted or monosubstituted or polysubstituted by halogen,
$R^3$ denotes hydrogen; $(C_1-C_8)$-alkyl; $(C_2-C_8)$-alkenyl or $(C_2-C_8)$-alkynyl,
$R^4$ denotes a heterocyclic radical of the formulae

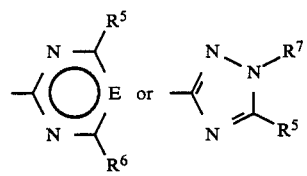

wherein E is CH or N,
n denotes 0, 1, 2 or 3,
$R^5$ and $R^6$, independently of one another, denote hydrogen; halogen; $(C_1-C_4)$-alkyl or $(C_1-C_4)$-alkoxy, both of which are unsubstituted or monosubstituted or polysubstituted by halogen; di-$(C_1-C_4)$-alkoxy-$(C_1-C_2)$-alkyl; cyclopropyl, —$OCHR^8COOR^9$; $NR^9R^{10}$ or $(C_1-C_4)$-alkylthio,
$R^7$ denotes $(C_1-C_4)$-alkyl,
$R^8$ denotes hydrogen or $(C_1-C_4)$-alkyl and
$R^9$ and $R^{10}$, independently of one another, denote hydrogen; $(C_1-C_4)$-alkyl; $(C_2-C_4)$-alkenyl or $(C_2-C_4)$-alkynyl.

It is possible for the compounds of the formula I to form salts in which the hydrogen of the —$SO_2$—NH— group is replaced by a cation which is suitable for agriculture. In general, these salts are metal salts, in particular alkali metal salts or alkaline earth metal salts, if appropriate, alkylated ammonium salts or organic amine salts. They are preferably prepared at temperatures of 0°–100° C. in inert solvents, such as, for example, water, methanol or acetone. Suitable bases for preparing the salts according to the invention are, for example, alkali metal carbonates, such as potassium carbonate, alkali metal and alkaline earth metal hydroxides, ammonia or ethanolamine.

Preferred compounds of the formula I are those in which $R^1$ denotes $(C_1-C_4)$-alkyl which is substituted as described above, or $(C_3-C_4)$-alkenyl which can be substituted as described above, or propargyl; $R^2$ denotes halogen, $(C_1-C_3)$-alkyl or $(C_1-C_3)$-alkoxy, both of which can be substituted as described above, where $R^2$ is preferably in the 3-position of the phenyl ring (relative to the radical $COOR^1$); n denotes 0, 1 or 2; $R^3$ denotes hydrogen, $(C_1-C_4)$-alkyl or allyl; $R^4$ denotes a radical of the formula

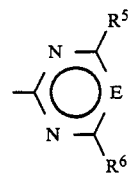

and $R^5$ and $R^6$ independently of one another denote halogen, $(C_1-C_4)$-alkyl or $(C_1-C_4)$-alkoxy, both of which can be substituted by halogen, and their salts.

Halogen preferably denotes fluorine, chlorine or bromine. Halogenated alkyl or halogenated alkoxy are in particular to be taken to mean the radicals $CF_3$, $CH_2$—$CH_2Cl$, $CH_2CH_2Br$, $CH_2CF_3$, $OCF_2H$ or $OCH_2CF_3$. Halogenated alkenyl or halogenated alkynyl denotes in particular $CH_2CH$=$CHCl$, $CH_2CCl$=$CCl_2$ or $CH_2$—$C$≡$CCH_2$—$Cl$.

Particularly preferred compounds of the formula (I) are those in which $R^1$ denotes $(C_1-C_4)$-alkyl which is substituted as described above, or $(C_3-C_4)$-alkenyl which can be substituted as described above, or propargyl, in particular allyl or propargyl; n denotes O; $R^3$ denotes hydrogen, $R^4$ denotes a radical of the formula

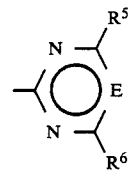

and $R^5$ and $R^6$ independently of one another denote chlorine, bromine, $(C_1-C_4)$-alkyl, $(C_1-C_4)$-alkoxy, $OCF_2H$, $OCH_2CF_3$ or $CF_3$, in particular $(C_1-C_2)$-alkyl or $(C_1-C_2)$-alkoxy, and their salts.

The invention furthermore relates to processes for the preparation of compounds of the general formula (I), wherein (a) a compound of the formula (II)

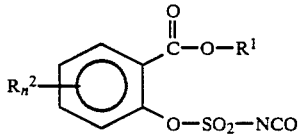 (II)

is reacted with a compound of the formula (III)

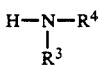 (III)

or (b) a compound of the formula (IV)

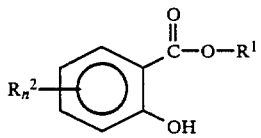 (IV)

is reacted with a chlorosulfonylurea of the formula (V)

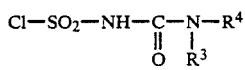 (V)

or (c) a substituted benzoic acid of the formula (VI)

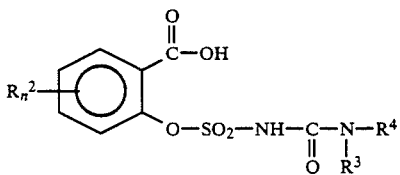 (VI)

is reacted with an alkylating reagent of the formula (VII)

 (VII)

where X stands for a nucleofugic leaving group, such as, for example, halogen, alkyl —SO$_2$—O— or tosyl.

The compounds of the formulae (II) and (III) are preferably reacted in inert aprotic solvents, such as, for example, acetonitrile, dichloromethane, toluene, tetrahydrofuran or dioxane, at temperatures between 0° C. and the boiling temperature of the solvent.

The phenoxysulfonylisocyanates of the formula (II) can be prepared in a simple manner by processes known in principle from the corresponding salicylates of the formula (IV) and chlorosulfonylisocyanate (cf. G. Lohaus, Chem. Ber. 105, 2791 (1972)).

The starting substances of the formula (III) are known or can be prepared by processes known in principle, for example by cyclizing corresponding guanidine derivatives with suitably substituted 1,3-diketones, cf., for example, "The Chemistry of Heterocyclic Compounds", Vol. XVI (1962) and Supplement I (1970), or by forming derivatives of cyanuric chloride, cf., for example, "The Chemistry of Heterocyclic Compounds", L. Rapaport: "s-Triazines and Derivatives" (1959).

The reaction of the compounds (IV) with the chlorosulfonylureas (V) is preferably carried out at temperatures between −10° C. and 80° C. in inert solvents, such as, for example, dichloromethane, tetrahydrofuran, dioxane or dimethoxyethane, in the presence of a base as the HCl-binding agent. Bases which can be employed are alkali metal or alkaline earth metal carbonates or bicarbonates, such as, for example, K$_2$CO$_3$, NaHCO$_3$ and Na$_2$CO$_3$, or tertiary amines, such as, for example, pyridine or triethylamine.

The salicylates (IV) are known from the literature or can be prepared by processes known from the literature. The chlorosulfonylureas (V) can be obtained from the amines of the formula (III) and chlorosulfonylisocyanate (EP-A No. 141,199).

The reaction of the benzoic acids (VI) with the reagents of the formula (VII) is carried out in inert solvents, such as, for example, dimethylformamide or dimethyl sulfoxide, preferably in the presence of an auxiliary base, such as, for example, triethylamine or tetramethylammonium hydroxide pentahydrate, at temperatures between 0° C. and the boiling temperature of the solvent.

The compounds of the formula I according to the invention have an excellent herbicidal activity against a broad range of economically important monocotyledon and dicotyledon weeds. The active substances act equally well on perennial weeds which produce shoots from rhizomes, rootstocks or other perennial organs and which cannot be easily controlled. In this context, it does not matter if the substances are applied before sowing, as a pre-emergence treatment or post-emergence treatment. Some representatives of the monocotyledon and dicotyledon weed flora which can be controlled by the compounds according to the invention may be mentioned individually as examples, but this is not taken to mean a restriction to certain species.

The monocotyledon weed species controlled include, for example, Avena, Lolium, Alopecurus, Phalaris, Echinochloa, Digitaria, Setaria etc. and cyperus species from the annual group, and of the perennial species include Agropyron, Cynodon, Imperata and Sorghum etc, and also perennial Cyperus species.

Of the dicotyledon weed species, the range of action covers species such as, for example, Galium, Viola, Veronica, Lamium, Stellaria, Amaranthus, Sinapis, Ipomoea, Matricaria, Abutilon, Sida etc from the annual plants, and Convolvulus, Cirsium, Rumex, Artemisia etc from the perennials.

Excellent control of weeds occurring under the specific culture conditions in rice, such as, for example, Sagittaria, Alisma, Eleocharis, Scirpus, Cyperus etc, by the active substances according to the invention is also possible.

If the compounds according to the invention are applied to the soil surface before germination, either emergence of the weed seedlings is prevented completely, or the weeds grow until they have reached the cotyledon stage but growth then comes to a standstill and, after a period of three to four weeks, the plants eventually die completely. When, in the post-emergence method, the active substances are applied to the green parts of the plants, growth also stops dramatically very soon after the treatment, and the weeds remain in the growth stage of the time of application, or, after a certain period of time, die more or less rapidly so that competition, of the weeds, which is detrimental for the crop plants can thus be prevented at a very early stage and in a sustained manner by using the novel compounds according to the invention.

Even though the compounds according to the invention have an excellent herbicidal activity against monocotyledon and dicotyledon weeds, crop plants of economically important crops such as, for example, wheat, barley, rye, rice, maize, sugar beet, cotton and soya beans, are damaged to a negligible extent only, or not at all. Thus, the present compounds are very suitable for selectively combating undesired plant growth in agricultural Nutz plantations.

In addition, the compounds according to the invention have plant growth-regulating properties in crop plants. They engage in the plant metabolism in a regulating manner and can thus be employed for facilitating harvesting, such as, for example, by provoking desiccation, abscission and reduced growth. Furthermore, they are suitable for generally regulating and inhibiting undesired vegetative growth, without simultaneously destroying the plants. Inhibition of vegetative growth plays an important role in many monocotyledon and dicotyledon crops because lodging can be reduced hereby, or prevented completely.

The agents according to the invention can be employed in the conventional preparations as wettable powders, emulsifiable concentrates, sprayable solutions, dusting agents, seed-dressing agents, dispersions, granules or microgranules.

Wettable powders are preparations which are uniformly dispersible in water and which, in addition to the active substance, also contain wetting agents, for example, polyoxyethylated alkylphenols, polyoxyethylated fatty alcohol alkylsulfonates or alkylphenylsulfonates, and dispersing agents, for example, sodium ligninsulfonate, sodium 2,2'-dinaphthylmethane-6,6'-disulfonate, sodium dibutylnaphthalenesulfonate or also sodium oleoylmethyltaurinate, and with the exception, if appropriate, of a diluent or inert substance. The formulations are prepared in a customary manner, for example by grinding and mixing of the components.

Emulsifiable concentrates can be prepared, for example, by dissolving the active substance in an inert organic solvent, for example butanol, cyclohexanone, dimethylformamide, xylene and also high-boiling aromatics or hydrocarbons, with the addition of one or more emulsifiers. In the case of liquid active substances, all or part of the solvent can be omitted. Emulsifiers which can be used are, for example: calcium salts of alkylarylsulfonic acid, such as Ca-dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, fatty alcohol/ propylene oxide/ethylene oxide condensation products alkyl polyglycol ethers, sorbitan fatty acid esters, polyoxyethylene sorbitan fatty acid esters or polyoxyethylene sorbitol esters.

Dusting agents are obtained by grinding the active substance with finely divided solid substances, for example talc or natural clays, such as kaolin, bentonite, pyrophillite or diatomaceous earth.

Granules can be produced either by spraying the active substance onto adsorptive, granulated inert material or by applying active substance concentrates onto the surface of excipients such as sand, kaolinite or granulated inert material, by means of binders, for example polyvinyl alcohol, sodium polyacrylate or alternatively mineral oils. Suitable active substances can also be granulated in the manner which is conventional for the preparation of fertilizer granules, if desired in a mixture with fertilizers.

The active substance concentration in wettable powders is, for example, about 10 to 90% by weight; the remainder to 100% by weight comprises conventional formulation components. In the case of emulsifiable concentrates, the active substance concentration can be about 5 to 80% by weight. Dust-form formulations usually contain 5 to 20% by weight of active substance, sprayable solutions about 2 to 20% by weight. In the case of granules, the active substance content depends partly on whether the active compound is liquid or solid and on which granulation auxiliaries, fillers etc are used.

In addition, the active substance formulations mentioned contain, if appropriate, the adhesives, wetting agents, dispersing agents, emulsifiers, penetrants, solvents, fillers or excipients which are conventional in each case.

For use, the concentrates, present in commercially available form, are diluted, if appropriate, in a conventional manner, for example using water in the case of wettable powders, emulsifiable concentrates, dispersions and, in some cases, also in the case of microgranules. Dust-form and granulated preparations and also sprayable solutions are usually not further diluted with inert substances before use.

The application rate required varies with the external conditions, such as temperature, humidity amongst others. It can vary within a wide range, for example from 0.005 to 10.0 kg/ha or more of active substance, preferably, however, it is from 0.01 to 5 kg/ha.

If appropriate, it is also possible to use mixtures or mixed formulations with other active substances, such as, for example, insecticides, acaricides, herbicides, fertilizers, growth regulators or fungicides.

The following examples illustrate the invention in more detail.

FORMULATION EXAMPLES

A. A dusting agent is obtained by mixing 10 parts by weight of active substance and 90 parts by weight of talc or inert substance, and comminuting the mixture in a hammer mill.

B. A wettable powder which is readily dispersible in water is obtained by mixing 25 parts by weight of active substance, 64 parts by weight of kaolin-containing quartz as inert substance, 10 parts by weight of potassium ligninsulfonate and 1 part by weight of sodium oleoylmethyltaurinate as wetting and dispersing agent, and grinding the mixture in a pinned disk mill.

C. A dispersion concentrate which is readily dispersible in water is obtained by mixing 20 parts by weight of active substance with 6 parts by weight of alkylphenol polyglycol ether (Triton X 207), 3 parts by weight of isotridecanol polyglycol ether (8 EO) and 71 parts by weight of paraffinic mineral oil (boiling range, for example, about 255° to above 377° C.), and grinding the mixture in a ball mill to a fineness of below 5 microns.

D. An emulsifiable concentrate is obtained from 15 parts by weight of active substance, 75 parts by weight of cyclohexanone as solvent and 10 parts by weight of oxyethylated nonylphenol (10 EO) as emulsifier.

CHEMICAL EXAMPLES

Example 1

Allyl 2-isocyanatosulfonyloxy-3-methyl-benzoate

A solution of 3.7 g (0.026 mole) of chlorosulfonylisocyanate in 25 ml of absolute toluene are added dropwise to a solution of 4.8 g (0.025 mole) of allyl 3-methylsalicylate in 25 ml of absolute toluene, at 25° C. When the dropwise addition is complete, the temperature is increased slowly to 110° C., and the mixture is refluxed for 6 hours. The mixture is cooled and the solvent is removed on a rotary evaporator. The yellow oil remaining (7.5 g≐100% of theory) is employed without further purification.

Example 2

Allyl 2-[3-(4-methoxy-6-methylpyrimidin-2-yl)ureidosulfonyloxy]-3-methylbenzoate A solution of 7.5 g (0.025 mole) of the product in Example 1 in 20 ml of dichloromethane are added dropwise to 3.5 g (0.025 mole) of 2-amino-4-methoxy-6-methyl-pyrimidine in 15 ml of dichloromethane, at 0° C. The mixture is allowed to warm to room temperature and is stirred for 24 hours. The reaction solution is diluted with 100 ml of dichloromethane and is washed with 50 ml of 1N hydrochloric acid and 50 ml of water. The organic phase is dried with sodium sulfate, and the solvent is removed on a rotary evaporator. The viscous oil remaining is crystallized by trituration with 1-chlorobutane. 7.4 g (68% of theory) of allyl 2-[3-(4-methoxy-6-methylpyrimidin-2-yl)-ureidosulfonyloxy]-3-methylbenzoate of melting point 127°–128° C. are obtained.

Example 3

2-Chloroethyl 2-[3-(4,6-dimethoxypyrimidin-2-yl)ureidosulfonyloxy]-benzoate 2.02 g (0.013 mole) of 2-amino-4,6-dimethoxypyrimidine are dissolved in 80 ml of dichloromethane, and 4.28 g (0.014 mole) of 2-chloroethyl 2-isocyanatosulfonyloxybenzoate, dissolved in 20 ml of dichloromethane, are added at 0° C. The reaction mixture is stirred at room temperature for 18 hours and is then stirred into 600 ml of n-heptane. In this manner, 4.72 g (79% of theory) of 2-chloroethyl 2-[3-(4,6-dimethoxypyrimidin-2-yl)ureidosulfonyloxy]-benzoate of melting point 148°–150° C. are obtained.

Example 4

Allyl 2-[3-(4,6-dimethoxypyrimidin-2-yl)ureidosulfonyloxy]-benzoate 1.55 g (0.01 mole) of 2-amino-4,6-dimethoxypyrimidine are dissolved in 100 ml of dichloromethane, and 3.40 g (0.012 mole) of allyl 2-isocyanatosulfonyloxybenzoate, dissolved in 20 ml of dichloromethane, are added at 0° C. The mixture is stirred at room temperature for 18 hours and filtered off with suction, and 2.54 g (58% of theory) of allyl 2-[3-(4,6-dimethoxypyrimidin-2-yl)ureidosulfonyloxy]-benzoate of melting point 110°–112° C. are obtained.

The compounds listed below can be prepared in an analogous manner.

TABLES 1a–c

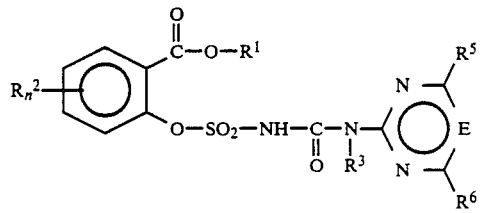

Table 1a: $(R^2)_n$ = H; $R^3$ = H

| Example No. | $R^1$ | $R^5$ | $R^6$ | E | m.p. [°C.] |
|---|---|---|---|---|---|
| 5 | CH$_2$CH$_2$Cl | CH$_3$ | CH$_3$ | CH | Oil |
| 6 | " | OCH$_3$ | CH$_3$ | CH | 56–60 |
| 7 | " | CH$_3$ | CH$_3$ | N | |
| 8 | " | OCH$_3$ | CH$_3$ | N | |
| 9 | " | OCH$_3$ | OCH$_3$ | N | |
| 10 | " | OCH$_3$ | Cl | CH | 132–135 |
| 11 | " | OCF$_2$H | CH$_3$ | CH | |
| 12 | " | OCF$_2$H | OCF$_2$H | CH | |
| 13 | " | OCH$_3$ | Br | CH | |
| 14 | " | CH$_3$ | Cl | CH | |
| 15 | " | OCH$_3$ | H | CH | |
| 16 | " | OCH$_3$ | NHCH$_3$ | CH | |
| 17 | " | OCH$_3$ | NHCH$_3$ | N | |
| 18 | " | CH$_3$ | NHCH$_3$ | CH | |
| 19 | " | CH$_3$ | NHCH$_3$ | N | |
| 20 | " | OCH$_3$ | SCH$_3$ | CH | |
| 21 | " | OCH$_3$ | OC$_2$H$_5$ | CH | |
| 22 | " | OCH$_3$ | OC$_3$H$_7$ | CH | |
| 23 | " | OCH$_3$ | OC$_2$H$_5$ | N | |
| 24 | " | Cl | OC$_2$H$_5$ | CH | |
| 25 | " | OC$_2$H$_5$ | OC$_2$H$_5$ | CH | |
| 26 | " | C$_2$H$_5$ | OCH$_3$ | CH | |
| 27 | " | CF$_3$ | OCH$_3$ | CH | |
| 28 | " | OCH$_2$CF$_3$ | CH$_3$ | CH | |
| 29 | " | OCH$_2$CF$_3$ | OCH$_3$ | CH | |
| 30 | " | OCH$_2$CF$_3$ | OCH$_2$CF$_3$ | CH | |
| 31 | " | OCH$_2$CF$_3$ | NHCH$_3$ | CH | |
| 32 | " | OCH$_2$CF$_3$ | OCH$_3$ | N | |
| 33 | " | OCH$_2$CF$_3$ | NHCH$_3$ | N | |
| 34 | " | OCH$_3$ | NHC$_2$H$_5$ | CH | |
| 35 | " | OCH$_2$CF$_3$ | NHC$_2$H$_5$ | CH | |
| 36 | " | OCH$_3$ | N(CH$_3$)$_2$ | CH | |
| 37 | " | OCH$_3$ | CH(OCH$_3$)$_2$ | CH | |
| 38 | CH$_2$CH$_2$OCH$_3$ | CH$_3$ | CH$_3$ | CH | |
| 39 | " | OCH$_3$ | CH$_3$ | CH | |
| 40 | " | CH$_3$ | CH$_3$ | N | |
| 41 | " | OCH$_3$ | CH$_3$ | N | |
| 42 | " | OCH$_3$ | OCH$_3$ | N | |
| 43 | " | OCH$_3$ | Cl | CH | |
| 44 | " | OCF$_2$H | CH$_3$ | CH | |
| 45 | " | OCF$_2$H | OCF$_2$H | CH | |
| 46 | " | OCH$_3$ | Br | CH | |
| 47 | " | CH$_3$ | Cl | CH | |
| 48 | " | OCH$_3$ | H | CH | |
| 49 | " | OCH$_3$ | NHCH$_3$ | CH | |
| 50 | " | OCH$_3$ | NHCH$_3$ | N | |
| 51 | " | CH$_3$ | NHCH$_3$ | CH | |
| 52 | " | CH$_3$ | NHCH$_3$ | N | |
| 53 | " | OCH$_3$ | SCH$_3$ | CH | |
| 54 | " | OCH$_3$ | OC$_2$H$_5$ | CH | |
| 55 | " | OCH$_3$ | OC$_3$H$_7$ | CH | |
| 56 | " | OCH$_3$ | OC$_2$H$_5$ | N | |
| 57 | " | Cl | OC$_2$H$_5$ | CH | |
| 58 | " | OC$_2$H$_5$ | OC$_2$H$_5$ | CH | |
| 59 | " | C$_2$H$_5$ | OCH$_3$ | CH | |
| 60 | " | CF$_3$ | OCH$_3$ | CH | |
| 61 | " | OCH$_2$CF$_3$ | CH$_3$ | CH | |
| 62 | " | OCH$_2$CF$_3$ | OCH$_3$ | CH | |
| 63 | " | OCH$_2$CF$_3$ | OCH$_2$CF$_3$ | CH | |
| 64 | " | OCH$_2$CF$_3$ | NHCH$_3$ | CH | |
| 65 | " | OCH$_2$CF$_3$ | OCH$_3$ | N | |
| 66 | " | OCH$_2$CF$_3$ | NHCH$_3$ | N | |
| 67 | " | OCH$_3$ | OCH$_3$ | CH | 131–133 |

TABLES 1a–c-continued

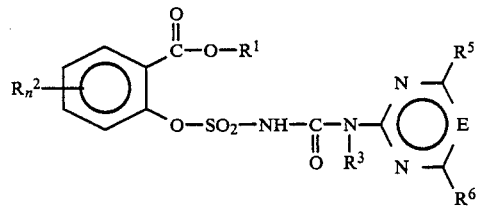
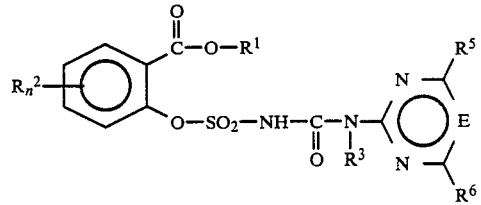

Table 1a: $(R^2)_n = H$; $R^3 = H$

| Example No. | $R^1$ | $R^5$ | $R^6$ | E | m.p. [°C.] |
|---|---|---|---|---|---|
| 68 | " | OCH$_2$CF$_3$ | NHC$_2$H$_5$ | CH | |
| 69 | " | OCH$_3$ | N(CH$_3$)$_2$ | CH | |
| 70 | " | OCH$_3$ | CH(OCH$_3$)$_2$ | CH | |
| 71 | CH$_2$CH=CH$_2$ | CH$_3$ | CH$_3$ | CH | |
| 72 | " | OCH$_3$ | CH$_3$ | CH | |
| 73 | " | CH$_3$ | CH$_3$ | N | |
| 74 | " | OCH$_3$ | CH$_3$ | N | Oil |
| 75 | " | OCH$_3$ | OCH$_3$ | N | |
| 76 | " | OCH$_3$ | Cl | CH | |
| 77 | " | OCF$_2$H | CH$_3$ | CH | |
| 78 | " | OCF$_2$H | OCF$_2$H | CH | |
| 79 | " | OCH$_3$ | Br | CH | |
| 80 | " | CH$_3$ | Cl | CH | |
| 81 | " | OCH$_3$ | H | CH | |
| 82 | " | OCH$_3$ | NHCH$_3$ | CH | |
| 83 | " | OCH$_3$ | NHCH$_3$ | N | |
| 84 | " | CH$_3$ | NHCH$_3$ | CH | |
| 85 | " | CH$_3$ | NHCH$_3$ | N | |
| 86 | " | OCH$_3$ | SCH$_3$ | CH | |
| 87 | " | OCH$_3$ | OC$_2$H$_5$ | CH | |
| 88 | " | OCH$_3$ | OC$_3$H$_7$ | CH | |
| 89 | " | OCH$_3$ | OC$_2$H$_5$ | N | |
| 90 | " | Cl | OC$_2$H$_5$ | CH | |
| 91 | " | OC$_2$H$_5$ | OC$_2$H$_5$ | CH | resin |
| 92 | " | C$_2$H$_5$ | OCH$_3$ | CH | |
| 93 | " | CF$_3$ | OCH$_3$ | CH | |
| 94 | " | OCH$_2$CF$_3$ | CH$_3$ | CH | |
| 95 | " | OCH$_2$CF$_3$ | OCH$_3$ | CH | |
| 96 | " | OCH$_2$CF$_3$ | OCH$_2$CF$_3$ | CH | |
| 97 | " | OCH$_2$CF$_3$ | NHCH$_3$ | CH | |
| 98 | " | OCH$_2$CF$_3$ | OCH$_3$ | N | |
| 99 | " | OCH$_2$CF$_3$ | NHCH$_3$ | N | |
| 100 | " | OCH$_3$ | NHC$_2$H$_5$ | CH | |
| 101 | " | OCH$_2$CF$_3$ | NHC$_2$H$_5$ | CH | |
| 102 | " | OCH$_3$ | N(CH$_3$)$_2$ | CH | |
| 103 | " | OCH$_3$ | CH(OCH$_3$)$_2$ | CH | |
| 104 | CH$_2$CF$_3$ | OCH$_3$ | OCH$_3$ | CH | 139–140 |
| 105 | " | CH$_3$ | CH$_3$ | CH | |
| 106 | " | OCH$_3$ | CH$_3$ | CH | |
| 107 | " | CH$_3$ | CH$_3$ | N | |
| 108 | " | OCH$_3$ | CH$_3$ | N | |
| 109 | " | OCH$_3$ | OCH$_3$ | N | |
| 110 | " | OCH$_3$ | Cl | CH | |
| 111 | " | OCF$_2$H | CH$_3$ | CH | |
| 112 | " | OCF$_2$H | OCF$_2$H | CH | |
| 113 | " | OCH$_3$ | Br | CH | |
| 114 | " | CH$_3$ | Cl | CH | |
| 115 | " | OCH$_3$ | H | CH | |
| 116 | " | OCH$_3$ | NHCH$_3$ | CH | |
| 117 | " | OCH$_3$ | NHCH$_3$ | N | |
| 118 | " | CH$_3$ | NHCH$_3$ | CH | |
| 119 | " | CH$_3$ | NHCH$_3$ | N | |
| 120 | " | OCH$_3$ | SCH$_3$ | CH | |
| 121 | " | OCH$_3$ | OC$_2$H$_5$ | CH | |
| 122 | " | OCH$_3$ | OC$_3$H$_7$ | CH | |
| 123 | " | OCH$_3$ | OC$_2$H$_5$ | N | |
| 124 | " | Cl | OC$_2$H$_5$ | CH | |
| 125 | " | OC$_2$H$_5$ | OC$_2$H$_5$ | CH | |
| 126 | " | C$_2$H$_5$ | OCH$_3$ | CH | |
| 127 | " | CF$_3$ | OCH$_3$ | CH | |
| 128 | " | OCH$_2$CF$_3$ | CH$_3$ | CH | |
| 129 | " | OCH$_2$CF$_3$ | OCH$_3$ | CH | |
| 130 | " | OCH$_2$CF$_3$ | OCH$_2$CF$_3$ | CH | |
| 131 | " | OCH$_2$CF$_3$ | NHCH$_3$ | CH | |
| 132 | " | OCH$_2$CF$_3$ | OCH$_3$ | N | |
| 133 | " | OCH$_2$CF$_3$ | NHCH$_3$ | N | |
| 134 | " | OCH$_3$ | NHC$_2$H$_5$ | CH | |
| 135 | " | OCH$_2$CF$_3$ | NHC$_2$H$_5$ | CH | |
| 136 | " | OCH$_3$ | N(CH$_3$)$_2$ | CH | |
| 137 | " | OCH$_3$ | CH(OCH$_3$)$_2$ | CH | |
| 138 | CH$_2$C≡CH | OCH$_3$ | OCH$_3$ | CH | 124–125 |
| 139 | " | OCH$_3$ | CH$_3$ | CH | 56–58 |
| 140 | " | OCH$_3$ | CH$_3$ | N | 60–62 |
| 141 | " | OCH$_3$ | OCH$_3$ | N | 144 |
| 142 | " | OCH$_3$ | Cl | CH | |
| 143 | " | OCF$_2$H | CH$_3$ | CH | |
| 144 | " | OCF$_2$H | OCF$_2$H | CH | |
| 145 | " | OCH$_3$ | NHCH$_3$ | CH | |
| 146 | " | Cl | OC$_2$H$_5$ | CH | |
| 147 | " | OCH$_2$CF$_3$ | OCH$_3$ | CH | |
| 148 | " | OCH$_2$CF$_3$ | OCH$_3$ | N | |
| 149 | CH$_2$CH=CHCl | OCH$_3$ | OCH$_3$ | CH | |
| 150 | " | OCH$_3$ | CH$_3$ | CH | |
| 151 | " | OCH$_3$ | CH$_3$ | N | |
| 152 | " | OCH$_3$ | OCH$_3$ | N | |
| 153 | " | OCH$_3$ | Cl | CH | |
| 154 | " | OCF$_2$H | CH$_3$ | CH | |
| 155 | " | OCF$_2$H | OCF$_2$H | CH | |
| 156 | " | OCH$_3$ | NHCH$_3$ | CH | |
| 157 | " | Cl | OC$_2$H$_5$ | CH | |
| 158 | " | OCH$_2$CF$_3$ | OCH$_3$ | CH | |
| 159 | " | OCH$_2$CF$_3$ | OCH$_3$ | N | |
| 160 | CH$_2$CCl=CCl$_2$ | OCH$_3$ | OCH$_3$ | CH | |
| 161 | " | OCH$_3$ | CH$_3$ | CH | |
| 162 | " | OCH$_3$ | CH$_3$ | N | |
| 163 | " | OCH$_3$ | OCH$_3$ | N | |
| 164 | " | OCH$_3$ | Cl | CH | |
| 165 | " | OCF$_2$H | CH$_3$ | CH | |
| 166 | " | OCF$_2$H | OCF$_2$H | CH | |
| 167 | " | OCH$_3$ | NHCH$_3$ | CH | |
| 168 | " | Cl | OC$_2$H$_5$ | CH | |
| 169 | " | OCH$_2$CF$_3$ | OCH$_3$ | CH | |
| 170 | " | OCH$_2$CF$_3$ | OCH$_3$ | N | |
| 171 | CH$_2$CH=CHCH$_3$ | OCH$_3$ | OCH$_3$ | CH | |
| 172 | " | OCH$_3$ | CH$_3$ | CH | |
| 173 | " | OCH$_3$ | CH$_3$ | N | |
| 174 | " | OCH$_3$ | OCH$_3$ | N | |
| 175 | " | OCH$_3$ | Cl | CH | |
| 176 | " | OCF$_2$H | CH$_3$ | CH | |
| 177 | " | OCF$_2$H | OCF$_2$H | CH | |
| 178 | " | OCH$_3$ | NHCH$_3$ | CH | |
| 179 | " | Cl | OC$_2$H$_5$ | CH | |
| 180 | " | OCH$_2$CF$_3$ | OCH$_3$ | CH | |
| 181 | " | OCH$_2$CF$_3$ | OCH$_3$ | N | |
| 182 | CH$_2$C≡CCH$_3$ | OCH$_3$ | OCH$_3$ | CH | |
| 183 | " | OCH$_3$ | CH$_3$ | CH | |
| 184 | " | OCH$_3$ | CH$_3$ | N | |
| 185 | " | OCH$_3$ | OCH$_3$ | N | |
| 186 | " | OCH$_3$ | Cl | CH | |
| 187 | " | OCF$_2$H | CH$_3$ | CH | |
| 188 | " | OCF$_2$H | OCF$_2$H | CH | |
| 189 | " | OCH$_3$ | NHCH$_3$ | CH | |
| 190 | " | Cl | OC$_2$H$_5$ | CH | |
| 191 | " | OCH$_2$CF$_3$ | OCH$_3$ | CH | |
| 192 | " | OCH$_2$CF$_3$ | OCH$_3$ | N | |
| 193 | CH$_2$CH$_2$Br | OCH$_3$ | OCH$_3$ | CH | |
| 194 | " | OCH$_3$ | CH$_3$ | CH | |
| 195 | " | OCH$_3$ | CH$_3$ | N | |

TABLES 1a-c-continued

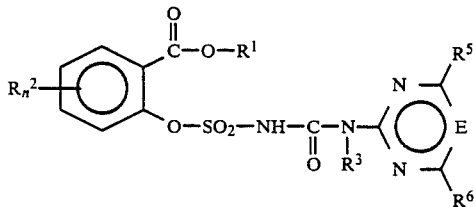

| | | | | |
|---|---|---|---|---|
| 196 | " | OCH₃ | OCH₃ | N |
| 197 | " | OCH₃ | Cl | CH |
| 198 | " | OCF₂H | CH₃ | CH |
| 199 | " | OCF₂H | OCF₂H | CH |
| 200 | " | OCH₃ | NHCH₃ | CH |
| 201 | " | Cl | OC₂H₅ | CH |
| 202 | " | OCH₂CF₃ | OCH₃ | CH |
| 203 | " | OCH₂CF₃ | OCH₃ | N |
| 204 | CH₂CH(OCH₃)₂ | OCH₃ | OCH₃ | CH |
| 205 | " | OCH₃ | CH₃ | CH |
| 206 | " | OCH₃ | CH₃ | N |

Table 1a: $(R^2)_n = H; R^3 = H$

| Example No. | $R^1$ | $R^5$ | $R^6$ | E | m.p. [°C.] |
|---|---|---|---|---|---|

TABLE 1b $R^3 = H$

| Example No. | $R^1$ | $(R^2)_n$ | $R^5$ | $R^6$ | E | m.p. |
|---|---|---|---|---|---|---|
| 207 | CH₂CH₂Cl | 3-CH₃ | OCH₃ | OCH₃ | CH | 154–156 |
| 208 | " | 3-CH₃ | OCH₃ | CH₃ | N | |
| 209 | " | 6-CH₃ | OCH₃ | OCH₃ | CH | |
| 210 | " | 6-CH₃ | OCH₃ | Cl | CH | |
| 211 | CH₂CH₂OCH₃ | 3-CH₃ | OCH₃ | OCH₃ | CH | |
| 212 | " | 3-CH₃ | OCH₃ | CH₃ | CH | |
| 213 | CH₂CH=CH₂ | 3-CH₃ | OCH₃ | OCH₂CF₃ | CH | |
| 214 | " | 3-CH₃ | OCH₃ | CH₃ | N | |
| 215 | " | 3-CH₃ | OCH₃ | OCH₃ | CH | 126–127 |
| 216 | " | 3-CH₃ | OCH₃ | Cl | CH | |
| 217 | " | 3-CH₃ | CH₃ | CH₃ | CH | 107–110 |
| 218 | " | 3-CH₃ | OCH₃ | Cl | N | |
| 219 | " | 3-CH₃ | OCH₃ | OCH₂CF₃ | N | |
| 220 | " | 3-CH₃ | OC₂H₅ | NHCH₃ | N | |
| 221 | CH₂CF₃ | 3-CH₃ | OCH₃ | OCH₃ | CH | |
| 222 | " | 3-CH₃ | OCH₃ | Cl | CH | |
| 223 | CH₂C≡CH | 3-CH₃ | OCH₃ | OCH₃ | CH | 126 |
| 224 | " | 6-CH₃ | OCF₂H | OCF₂H | CH | |
| 225 | CH₂CH=CHCl | 3-CH₃ | OCH₃ | OCH₃ | CH | |
| 226 | " | 6-CH₃ | OCH₃ | CH₃ | N | |
| 227 | CH₂CH₂Cl | 3-OCH₃ | OCH₃ | OCH₃ | CH | |
| 228 | " | 3-OCH₃ | OCH₃ | Cl | CH | |
| 229 | " | 6-OCH₃ | OCH₃ | OCH₃ | CH | |
| 230 | " | 6-OCH₃ | OCH₂CF₃ | OCH₃ | CH | |
| 231 | CH₂CH₂OCH₃ | 3-OCH₃ | OCH₃ | OCH₃ | CH | |
| 232 | " | 3-OCH₃ | OCH₃ | CH₃ | N | |
| 233 | CH₂CH=CH₂ | 3-OCH₃ | CH₃ | CH₃ | CH | 151–152 |
| 234 | " | 3-OCH₃ | OCH₃ | CH₃ | CH | 132–133 |
| 235 | " | 3-OCH₃ | OCH₃ | OCH₃ | CH | 138–139 |
| 236 | " | 3-OCH₃ | OCH₂CF₃ | OCH₃ | CH | |
| 237 | " | 3-OCH₃ | OCH₃ | Cl | CH | |
| 238 | " | 3-OCH₃ | OCH₃ | CH₃ | N | 135–136 |
| 239 | CH₂CH=CH₂ | 3-OCH₃ | OCH₃ | Cl | N | |
| 240 | " | 3-OCH₃ | OCH₃ | OCH₂CF₃ | N | |
| 241 | " | 3-OCH₃ | OC₂H₅ | NHCH₃ | N | |
| 242 | CH₂CF₃ | 3-OCH₃ | OCH₃ | Cl | CH | |
| 243 | " | 3-OCH₃ | OCH₃ | OCH₃ | CH | |
| 244 | " | 6-OCH₃ | OCH₃ | CH₃ | CH | |
| 245 | CH₂CH₂Br | 3-OCH₃ | OCH₃ | OCH₃ | CH | |
| 246 | " | 6-OCH₃ | OCH₃ | CH₃ | N | |
| 247 | CH₂CH₂Cl | 3-Cl | OCH₃ | OCH₃ | CH | |
| 248 | " | 3-Cl | OCH₃ | Cl | CH | |
| 249 | " | 4-Cl | OCH₃ | OCH₃ | CH | |
| 250 | " | 4-Cl | OCF₂H | CH₃ | CH | |
| 251 | " | 5-Cl | OCH₃ | OCH₃ | CH | |
| 252 | " | 5-Cl | OCH₃ | CH₃ | N | |
| 253 | " | 6-Cl | OCH₃ | OCH₃ | CH | |
| 254 | " | 6-Cl | OCH₃ | Cl | CH | |
| 255 | CH₂CH₂OCH₃ | 3-Cl | OCH₃ | OCH₃ | CH | |
| 256 | " | 3-Cl | OCF₂H | OCF₂H | CH | |
| 257 | " | 4-Cl | OCH₃ | OCH₃ | CH | |
| 258 | " | 4-Cl | OCH₃ | CH₃ | N | |
| 259 | " | 5-Cl | OCH₃ | OCH₃ | CH | |
| 260 | " | 5-Cl | OCH₃ | Cl | CH | |
| 261 | " | 6-Cl | OCH₃ | OCH₃ | CH | |
| 262 | CH₂CH=CH₂ | 4-Cl | OCH₂CF₃ | OCH₃ | CH | |
| 263 | " | 4-Cl | OCH₃ | OCH₃ | CH | 104–106 |
| 264 | " | 4-Cl | OCH₃ | CH₃ | N | |
| 265 | " | 4-Cl | CH₃ | CH₃ | CH | 93–95 |
| 266 | " | 4-Cl | OCH₃ | Cl | CH | |
| 267 | " | 4-Cl | OCH₃ | CH₃ | CH | 121–124 |
| 268 | " | 4-Cl | OCH₂CF₃ | OCH₃ | N | |
| 269 | " | 4-Cl | OCH₃ | Cl | N | |

TABLE 1b-continued $R^3 = H$

| Example No. | $R^1$ | $(R^2)_n$ | $R^5$ | $R^6$ | E | m.p. |
|---|---|---|---|---|---|---|
| 270 | " | 4-Cl | OC$_2$H$_5$ | NHCH$_3$ | N | |
| 271 | CH$_2$CH=CH$_2$ | 5-Cl | OCH$_3$ | OCH$_3$ | CH | 138 |
| 272 | " | 5-Cl | OCH$_3$ | CH$_3$ | N | 136 |
| 273 | " | 5-Cl | CH$_3$ | CH$_3$ | CH | 110–112 |
| 274 | " | 5-Cl | CH$_3$ | Cl | CH | 108–109 |
| 275 | " | 5-Cl | OCH$_3$ | CH$_3$ | CH | |
| 276 | " | 5-Cl | OCH$_3$ | OCH$_2$CF$_3$ | CH | |
| 277 | " | 5-Cl | OCH$_3$ | Cl | N | |
| 278 | " | 5-Cl | OCH$_3$ | OCH$_2$CF$_3$ | N | |
| 279 | CH$_2$CF$_3$ | 3-Cl | OCH$_3$ | OCH$_3$ | CH | |
| 280 | " | 4-Cl | OCH$_3$ | Cl | CH | |
| 281 | " | 5-Cl | OCH$_3$ | OCH$_3$ | CH | |
| 282 | " | 6-Cl | OCF$_2$H | CH$_3$ | CH | |
| 283 | CH$_2$CH=CHCH$_3$ | 3-Cl | OCH$_3$ | OCH$_3$ | CH | |
| 284 | " | 4-Cl | OCH$_3$ | CH$_3$ | N | |
| 285 | " | 5-Cl | OCH$_3$ | OCH$_3$ | CH | |
| 286 | " | 6-Cl | OCH$_3$ | Cl | CH | |
| 287 | CH$_2$CH$_2$Cl | 3-F | OCH$_3$ | OCH$_3$ | CH | |
| 288 | " | 3-F | OCF$_2$H | OCF$_2$H | CH | |
| 289 | " | 4-F | OCH$_3$ | OCH$_3$ | CH | |
| 290 | " | 4-F | OCH$_3$ | CH$_3$ | N | |
| 291 | " | 5-F | OCH$_3$ | OCH$_3$ | CH | |
| 292 | " | 5-F | OCH$_3$ | Cl | CH | |
| 293 | " | 6-F | OCH$_3$ | OCH$_3$ | CH | |
| 294 | " | 6-F | OCH$_2$CF$_3$ | OCH$_3$ | CH | |
| 295 | CH$_2$CH=CH$_2$ | 3-F | OCH$_3$ | OCH$_3$ | CH | 154 |
| 296 | " | 3-Cl | OCH$_3$ | CH$_3$ | N | |
| 297 | " | 4-F | OCH$_3$ | OCH$_3$ | CH | 93 |
| 298 | " | 4-F | OCH$_3$ | Cl | CH | |
| 299 | " | 5-F | OCH$_3$ | OCH$_3$ | CH | 145–146 |
| 300 | " | 5-F | OCH$_2$CF$_3$ | OCH$_3$ | N | 103–105 |
| 301 | " | 6-F | OCH$_3$ | OCH$_3$ | CH | |
| 302 | " | 6-Cl | OCH$_3$ | OCH$_3$ | N | |
| 303 | CH$_2$CH$_2$OCH$_3$ | 3-F | OCH$_3$ | OCH$_3$ | CH | |
| 304 | " | 3-F | OCH$_3$ | CH$_3$ | N | |
| 305 | " | 4-F | OCH$_3$ | OCH$_3$ | CH | |
| 306 | " | 4-F | OCH$_3$ | Cl | CH | |
| 307 | " | 5-F | OCH$_3$ | OCH$_3$ | CH | |
| 308 | " | 5-F | OCH$_3$ | CH$_3$ | CH | |
| 309 | " | 6-F | OCH$_3$ | OCH$_3$ | CH | |
| 310 | " | 6-F | OCH$_3$ | CH$_3$ | N | |
| 311 | CH$_2$CF$_3$ | 3-F | OCH$_3$ | OCH$_3$ | CH | |
| 312 | " | 3-F | OCH$_3$ | Cl | CH | |
| 313 | " | 4-F | OCH$_3$ | OCH$_3$ | CH | |
| 314 | " | 4-F | OCF$_2$H | CH$_3$ | CH | |
| 315 | " | 5-F | OCH$_3$ | OCH$_3$ | CH | |
| 316 | " | 5-F | OCH$_3$ | CH$_3$ | N | |
| 317 | " | 6-F | OCH$_3$ | OCH$_3$ | CH | |
| 318 | " | 6-F | OCH$_3$ | Cl | CH | |
| 319 | CH$_2$C≡CH | 3-F | OCH$_3$ | OCH$_3$ | CH | |
| 320 | " | 4-F | OCF$_2$H | OCF$_2$H | CH | |
| 321 | " | 5-F | OCH$_3$ | OCH$_3$ | CH | |
| 322 | " | 6-F | OCH$_3$ | CH$_3$ | N | |
| 323 | CH$_2$CH=CHCl | 3-F | OCH$_3$ | OCH$_3$ | CH | |
| 324 | " | 4-F | OCH$_3$ | Cl | CH | |
| 325 | " | 5-F | OCH$_3$ | OCH$_3$ | CH | |
| 326 | " | 6-F | OCH$_2$CF$_3$ | OCH$_3$ | CH | |
| 327 | CH$_2$CH$_2$Cl | 3-CF$_3$ | OCH$_3$ | OCH$_3$ | CH | |
| 328 | " | 3-CF$_3$ | OCH$_3$ | CH$_3$ | N | |
| 329 | " | 4-CF$_3$ | OCH$_3$ | OCH$_3$ | CH | |
| 330 | " | 4-CF$_3$ | OCH$_3$ | Cl | CH | |
| 331 | " | 5-CF$_3$ | OCH$_3$ | OCH$_3$ | CH | |
| 332 | " | 5-CF$_3$ | OCH$_2$CF$_3$ | OCH$_3$ | N | |
| 333 | " | 6-CF$_3$ | OCH$_3$ | OCH$_3$ | CH | |
| 334 | " | 6-CF$_3$ | OCH$_3$ | OCH$_3$ | N | |
| 335 | CH$_2$CH$_2$OCH$_3$ | 3-CF$_3$ | OCH$_3$ | OCH$_3$ | CH | |
| 336 | " | 3-CF$_3$ | OCH$_3$ | CH$_3$ | N | |
| 337 | " | 4-CF$_3$ | OCH$_3$ | OCH$_3$ | CH | |
| 338 | " | 4-CF$_3$ | OCH$_3$ | Cl | CH | |
| 339 | " | 5-CF$_3$ | OCH$_3$ | OCH$_3$ | CH | |
| 340 | " | 5-CF$_3$ | OCH$_3$ | CH$_3$ | CH | |
| 341 | " | 6-CF$_3$ | OCH$_3$ | OCH$_3$ | CH | |
| 342 | " | 6-CF$_3$ | OCH$_3$ | CH$_3$ | N | |
| 343 | CH$_2$CF$_3$ | 3-CF$_3$ | OCH$_3$ | OCH$_3$ | CH | |
| 344 | " | 3-CF$_3$ | OCH$_3$ | Cl | CH | |
| 345 | " | 4-CF$_3$ | OCH$_3$ | OCH$_3$ | CH | |
| 346 | " | 4-CF$_3$ | OCF$_2$H | CH$_3$ | CH | |
| 347 | " | 5-CF$_3$ | OCH$_3$ | OCH$_3$ | CH | |
| 348 | " | 5-CF$_3$ | OCH$_3$ | CH$_3$ | N | |

TABLE 1b-continued

R³ = H

| Example No. | R¹ | (R²)ₙ | R⁵ | R⁶ | E | m.p. |
|---|---|---|---|---|---|---|
| 349 | " | 6 CF₃ | OCH₃ | OCH₃ | CH | |
| 350 | " | 6-CF₃ | OCH₃ | Cl | CH | |
| 351 | CH₂CH=CH₂ | 3-CF₃ | OCH₃ | OCH₃ | CH | |
| 352 | " | 3-CF₃ | OCF₂H | OCF₂H | CH | |
| 353 | " | 4-CF₃ | OCH₃ | OCH₃ | CH | |
| 354 | " | 4-CF₃ | OCH₃ | CH₃ | N | |
| 355 | " | 5-CF₃ | OCH₃ | OCH₃ | CH | |
| 356 | " | 5-CF₃ | OCH₃ | Cl | CH | |
| 357 | " | 6-CF₃ | OCH₃ | OCH₃ | CH | |
| 358 | " | 6-CF₃ | OCH₂CF₃ | OCH₃ | CH | |
| 359 | CH₂CH₂Br | 3 CF₃ | OCH₃ | OCH₃ | CH | |
| 360 | " | 4-CF₃ | OCH₃ | CH₃ | N | |
| 361 | " | 5-CF₃ | OCH₃ | OCH₃ | CH | |
| 362 | " | 6-CF₃ | OCH₃ | Cl | CH | |
| 363 | CH₂C≡CCH₃ | 3-CF₃ | OCH₃ | OCH₃ | CH | |
| 364 | " | 4-CF₃ | OCH₂CF₃ | OCH₃ | N | |
| 365 | " | 5-CF₃ | OCH₃ | OCH₃ | CH | |
| 366 | " | 6-CF₃ | OCH₃ | OCH₃ | N | |
| 367 | CH₂CH₂OCH₃ | 4-OCF₂H | OCH₃ | OCH₃ | CH | |
| 368 | " | 4-OCF₂H | OCH₃ | CH₃ | N | |
| 369 | CH₂CH₂Cl | 4-OCF₂H | OCH₃ | OCH₃ | CH | |
| 370 | " | 4-OCF₂H | OCH₃ | Cl | CH | |
| 371 | CH₂CH=CH₂ | 4-OCF₂H | OCH₃ | OCH₃ | CH | |
| 372 | " | 4-OCF₂H | OCH₃ | CH₃ | CH | |
| 373 | CH₂—CF₃ | 4-OCF₂H | OCH₃ | OCH₃ | CH | |
| 374 | " | 4-OCF₂H | OCH₃ | CH₃ | N | |
| 375 | CH₂CH₂Cl | 3-NO₂ | OCH₃ | OCH₃ | CH | |
| 376 | " | 3-NO₂ | OCH₃ | Cl | CH | |
| 377 | " | 4-NO₂ | OCH₃ | OCH₃ | CH | |
| 378 | " | 4-NO₂ | OCF₂H | CH₃ | CH | |
| 379 | " | 5-NO₂ | OCH₃ | OCH₃ | CH | |
| 380 | " | 5-NO₂ | OCH₃ | CH₃ | N | |
| 381 | " | 6-NO₂ | OCH₃ | OCH₃ | CH | |
| 382 | " | 6-NO₂ | OCH₃ | Cl | CH | |
| 383 | CH₂CH=CH₂ | 3-NO₂ | OCH₃ | OCH₃ | CH | |
| 384 | " | 3 NO₂ | OCF₂H | OCF₂H | CH | |
| 385 | " | 4-NO₂ | OCH₃ | OCH₃ | CH | |
| 386 | " | 4-NO₂ | OCH₃ | CH₃ | N | |
| 387 | " | 5-NO₂ | OCH₃ | OCH₃ | CH | |
| 388 | " | 5-NO₂ | OCH₃ | Cl | CH | |
| 389 | " | 6-NO₂ | OCH₃ | OCH₃ | CH | |
| 390 | " | 6-NO₂ | OCH₂CF₃ | OCH₃ | CH | |
| 391 | CH₂CH₂OCH₃ | 3-NO₂ | OCH₃ | OCH₃ | CH | |
| 392 | " | 3-NO₂ | OCH₃ | CH₃ | N | |
| 393 | " | 4-NO₂ | OCH₃ | OCH₃ | CH | |
| 394 | " | 4-NO₂ | OCH₃ | Cl | CH | |
| 395 | " | 5-NO₂ | OCH₃ | OCH₃ | CH | |
| 396 | " | 5-NO₂ | OCH₂CF₃ | OCH₃ | N | |
| 397 | " | 6-NO₂ | OCH₃ | OCH₃ | CH | |
| 398 | " | 6-NO₂ | OCH₃ | OCH₃ | N | |
| 399 | CH₂CF₃ | 3-NO₂ | OCH₃ | OCH₃ | CH | |
| 400 | " | 3-NO₂ | OCH₃ | CH₃ | N | |
| 401 | " | 4-NO₂ | OCH₃ | OCH₃ | CH | |
| 402 | " | 4-NO₂ | OCH₃ | Cl | CH | |
| 403 | " | 5-NO₂ | OCH₃ | OCH₃ | CH | |
| 404 | " | 5-NO₂ | OCH₃ | CH₃ | CH | |
| 405 | " | 6-NO₂ | OCH₃ | OCH₃ | CH | |
| 406 | " | 6-NO₂ | OCH₃ | CH₃ | N | |
| 407 | CH₂C≡CH | 3-NO₂ | OCH₃ | OCH₃ | CH | |
| 408 | " | 4-NO₂ | OCH₃ | Cl | CH | |
| 409 | " | 5-NO₂ | OCH₃ | OCH₃ | CH | |
| 410 | " | 6-NO₂ | OCF₂H | CH₃ | CH | |
| 411 | CH₂CH=CHCl | 3-NO₂ | OCH₃ | OCH₃ | CH | |
| 412 | " | 4-NO₂ | OCH₃ | CH₃ | N | |
| 413 | " | 5-NO₂ | OCH₃ | OCH₃ | CH | |
| 414 | " | 6-NO₂ | OCH₃ | Cl | CH | |
| 415 | CH₂CH=CH₂ | 3,5-Cl₂ | OCH₃ | OCH₃ | CH | |
| 416 | " | 3,5-Cl₂ | OCF₂H | OCF₂H | CH | |
| 417 | " | 4,6-Cl₂ | OCH₃ | OCH₃ | CH | |
| 418 | " | 3,5-Cl₂ | OCH₃ | CH₃ | N | |
| 419 | " | 3,5-F₂ | OCH₃ | OCH₃ | CH | |
| 420 | " | 3,5-F₂ | OCH₃ | Cl | CH | |
| 421 | " | 4,6-F₂ | OCH₃ | OCH₃ | CH | |
| 422 | " | 3,5-F₂ | OCH₂CF₃ | OCH₃ | CH | |
| 423 | CH₂CH₂OCH₃ | 3,5-Cl₂ | OCH₃ | OCH₃ | CH | |
| 424 | " | 3,5-Cl₂ | OCH₃ | CH₃ | N | |
| 425 | " | 4,6-Cl₂ | OCH₃ | OCH₃ | CH | |
| 426 | " | 3,5-Cl₂ | OCH₃ | Cl | CH | |
| 427 | " | 3,5-F₂ | OCH₃ | OCH₃ | CH | |

TABLE 1b-continued

R³ = H

| Example No. | R¹ | (R²)ₙ | R⁵ | R⁶ | E | m.p. |
|---|---|---|---|---|---|---|
| 428 | " | 3,5-F₂ | OCH₂CF₃ | OCH₃ | N | |
| 429 | " | 4,6-F₂ | OCH₃ | OCH₃ | CH | |
| 430 | " | 3,5-F₂ | OCH₃ | OCH₃ | N | |
| 431 | CH₂CF₃ | 3,5-Cl₂ | OCH₃ | OCH₃ | CH | |
| 432 | " | 3,5-Cl₂ | OCH₃ | CH₃ | N | |
| 433 | " | 4,6-Cl₂ | OCH₃ | OCH₃ | CH | |
| 434 | " | 3,5-Cl₂ | OCH₃ | Cl | CH | |
| 435 | " | 3,5-F₂ | OCH₃ | OCH₃ | CH | |
| 436 | " | 3,5-F₂ | OCH₃ | CH₃ | CH | |
| 437 | " | 4,6-F₂ | OCH₃ | OCH₃ | CH | |
| 438 | " | 3,5-F₂ | OCH₃ | CH₃ | N | |
| 439 | CH₂CH₂Cl | 3,5-Cl₂ | OCH₃ | OCH₃ | CH | |
| 440 | " | 3,5-Cl₂ | OCH₃ | Cl | CH | |
| 441 | " | 4,6-Cl₂ | OCH₃ | OCH₃ | CH | |
| 442 | " | 3,5-Cl₂ | OCF₂H | CH₃ | CH | |
| 443 | " | 3,5-F₂ | OCH₃ | OCH₃ | CH | |
| 444 | " | 3,5-F₂ | OCH₃ | CH₃ | N | |
| 445 | " | 4,6-F₂ | OCH₃ | OCH₃ | CH | |
| 446 | " | 3,5-F₂ | OCH₃ | Cl | CH | |
| 447 | CH₂CCl=CCl₂ | 3,5-Cl₂ | OCH₃ | OCH₃ | CH | |
| 448 | " | 3,5-Cl₂ | OCF₂H | OCF₂H | CH | |
| 449 | " | 3,5-F₂ | OCH₃ | OCH₃ | CH | |
| 450 | " | 3,5-F₂ | OCH₃ | CH₃ | N | |
| 451 | CH₂C≡CCH₃ | 3,5-Cl₂ | OCH₃ | OCH₃ | CH | |
| 452 | " | 3,5-Cl₂ | OCH₃ | Cl | CH | |
| 453 | " | 3,5-F₂ | OCH₃ | OCH₃ | CH | |
| 454 | " | 3,5-F₂ | OCH₂CF₃ | OCH₃ | CH | |
| 455 | CH₂CH=CH₂ | 3-Cl | OCH₃ | OCH₃ | CH | 131–133 |
| 456 | " | 3-Cl | OCH₃ | CH₃ | CH | 77–82 |
| 457 | " | 3-C₂H₅ | CH₃ | Cl | CH | Glass |
| 458 | " | 3-C₂H₅ | OC₂H₅ | NHCH₃ | N | 133–135 |
| 459 | " | 3-C₂H₅ | OCH₃ | OCH₂CF₃ | N | 89–93 |
| 460 | " | 3-C₂H₅ | OCH₃ | CH₃ | N | Glass |
| 461 | " | 3-C₂H₅ | OCH₃ | CH₃ | CH | 136 |
| 462 | " | 3-C₂H₅ | OCH₃ | OCH₃ | CH | 76–78 |
| 463 | " | 4-F | OCH₃ | CH₃ | CH | 93–99 |
| 464 | " | 3-F | OCH₃ | CH₃ | CH | |
| 465 | " | 3-F | OCH₃ | CH₃ | N | |
| 466 | CH₂C≡CH | 3-CH₃ | OCH₃ | CH₃ | CH | 167–169 |
| 467 | " | 3-CH₃ | OCH₃ | CH₃ | N | 127–133(Zers.) |
| 468 | " | 3-OCH₃ | OCH₃ | OCH₃ | CH | 186 |
| 469 | " | 3-OCH₃ | OCH₃ | CH₃ | CH | 158–159 |
| 470 | " | 3-OCH₃ | OCH₃ | CH₃ | N | 141–143 |
| 471 | " | 3-Cl | OCH₃ | OCH₃ | CH | |
| 472 | " | 3-Cl | OCH₃ | CH₃ | CH | |
| 473 | " | 3-Cl | OCH₃ | CH₃ | N | |
| 474 | " | H | CH₃ | CH₃ | CH | 125–126 |
| 475 | " | H | OC₂H₅ | NHCH₃ | N | 132–134 |
| 476 | " | 3-F | OCH₃ | CH₃ | CH | |
| 477 | " | 6-F | OCH₃ | OCH₃ | CH | |

TABLE 1c

| Example No. | R¹ | (R²)ₙ | R³ | R⁵ | R⁶ | E | m.p. |
|---|---|---|---|---|---|---|---|
| 478 | CH₂CH₂Cl | H | CH₃ | OCH₃ | OCH₃ | CH | |
| 479 | " | H | CH₃ | OCH₃ | CH₃ | N | |
| 480 | " | H | CH₂CH=CH₂ | OCH₃ | OCH₃ | CH | |
| 481 | " | H | CH₂CH=CH₂ | OCH₃ | Cl | CH | |
| 482 | CH₂CH₂OCH₃ | H | CH₃ | OCH₃ | OCH₃ | CH | |
| 483 | " | H | CH₃ | OCH₃ | CH₃ | CH | |
| 484 | " | H | CH₂CH=CH₂ | OCH₃ | OCH₃ | CH | |
| 485 | " | H | CH₂CH=CH₂ | OCH₃ | CH₃ | N | |
| 486 | CH₂CH=CH₂ | H | CH₃ | OCH₃ | OCH₃ | CH | |
| 487 | " | H | CH₃ | OCH₃ | Cl | CH | |
| 488 | " | H | CH₂CH=CH₂ | OCH₃ | OCH₃ | CH | |
| 489 | " | H | CH₂CH=CH₂ | OCF₂H | CH₃ | CH | |
| 490 | CH₂CF₃ | H | CH₃ | OCH₃ | OCH₃ | CH | |
| 491 | " | H | CH₃ | OCH₃ | CH₃ | N | |
| 492 | " | H | CH₂CH=CH₂ | OCH₃ | OCH₃ | CH | |
| 493 | " | H | CH₂CH=CH₂ | OCH₃ | Cl | CH | |
| 494 | CH₂C≡CH | H | CH₃ | OCH₃ | OCH₃ | CH | |
| 495 | " | H | CH₂CH=CH₂ | OCF₂H | OCF₂H | CH | |
| 496 | CH₂CH=CHCl | H | CH₂CH=CH₂ | OCH₃ | OCH₃ | CH | |
| 497 | " | H | CH₃ | OCH₃ | CH₃ | N | |
| 498 | CH₂CH₂Cl | H | C₂H₅ | OCH₃ | OCH₃ | CH | |
| 499 | CH₂CH₂OCH₃ | H | C₂H₅ | OCH₃ | Cl | CH | |

TABLE 1c-continued

| Example No. | R¹ | (R²)$_n$ | R³ | R⁵ | R⁶ | E | m.p. |
|---|---|---|---|---|---|---|---|
| 500 | CH$_2$CH=CH$_2$ | H | C$_2$H$_5$ | OCH$_3$ | OCH$_3$ | CH | |
| 501 | CH$_2$CF$_3$ | H | C$_2$H$_5$ | OCH$_2$CF$_3$ | OCH$_3$ | CH | |
| 502 | CH$_2$C≡CH | H | C$_2$H$_5$ | OCH$_3$ | OCH$_3$ | CH | |
| 503 | CH$_2$CH$_2$Cl | 3-CH$_3$ | CH$_3$ | OCH$_3$ | CH$_3$ | N | |
| 504 | CH$_2$CH$_2$OCH$_3$ | 3-OCH$_3$ | CH$_3$ | OCH$_3$ | OCH$_3$ | CH | |
| 505 | CH$_2$CH=CH$_2$ | 4-Cl | CH$_2$CH=CH$_2$ | OCH$_3$ | Cl | CH | |
| 506 | CH$_2$CF$_3$ | 6-F | CH$_2$CH=CH$_2$ | OCH$_3$ | OCH$_3$ | CH | |
| 507 | CH$_2$C≡CH | 5-CF$_3$ | CH$_3$ | OCH$_2$CF$_3$ | OCH$_3$ | N | |

TABLE 2

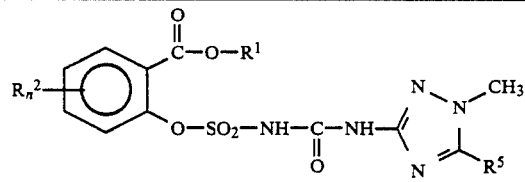

| Example No | R¹ | (R²)$_n$ | R⁵ | m.p. |
|---|---|---|---|---|
| 508 | CH$_2$CH=CH$_2$ | H | CH$_3$ | |
| 509 | " | H | H | |
| 510 | " | H | OCH$_3$ | |
| 511 | CH$_2$CH$_2$Cl | H | OCH$_3$ | |
| 512 | CH$_2$CH$_2$OCH$_3$ | H | OCH$_3$ | |
| 513 | CH$_2$C≡CH | H | OCH$_3$ | |
| 514 | CH$_2$CF$_3$ | H | OCH$_3$ | |
| 515 | CH$_2$CH=CHCl | H | OCH$_3$ | |
| 516 | CH$_2$CCl=CCl$_2$ | H | OCH$_3$ | |
| 517 | CH$_2$CH$_2$Br | H | OCH$_3$ | |
| 518 | CH$_2$CH=CHCH$_3$ | H | OCH$_3$ | |
| 519 | CH$_2$C≡CCH$_3$ | H | OCH$_3$ | |
| 520 | CH$_2$CH=CH$_2$ | 3-CH$_3$ | OCH$_3$ | |
| 521 | CH$_2$CH$_2$Cl | 3-OCH$_3$ | OCH$_3$ | |
| 522 | CH$_2$CH$_2$OCH$_3$ | 4-Cl | OCH$_3$ | |
| 523 | CH$_2$CF$_3$ | 5-CF$_3$ | OCH$_3$ | |
| 524 | CH$_2$C≡CH | 6-F | OCH$_3$ | |
| 525 | CH$_2$CH=CHCH$_3$ | 4-OCF$_2$H | OCH$_3$ | |

Biological Examples

The damage on the weeds and the tolerance by crop plants were scored using a key where numbers from 0 to 5 express the activity. In this key 0 denotes no action
1 denotes 0–20% action or damage
2 denotes 20–40% action or damage
3 denotes 40–60% action or damage
4 denotes 60–80% action or damage
5 denotes 80–100% action or damage 1. Pre-emergence action on weeds Seeds or rhizome pieces of monocotyledon and dicotyledon weeds were placed in plastic pots containing sandy loam and covered with soil. Various dosages of aqueous suspensions or emulsions of the compounds according to the invention formulated as wettable powders or emulsion concentrates were then applied to the surface of the cover soil, at an application rate of water of 600–800 /l ha (converted).

After the treatment, the pots were placed in the greenhouse and maintained at good growth conditions for the weeds. Visual scoring of the damage to plants or the emergence damage was carried out after the emergence of the test plants after a trial period of 3–4 weeks, comparing them to untreated control plants. As shown by the score data in Table 2a, the compounds according to the invention have good herbicidal pre-emergence activity against a broad range of weed grasses and broad-leaf weeds.

2. Post-emergence action on weeds

Seeds or rhizome pieces of monocotyledon and dicotyledon weeds were placed in plastic pots in sandy loam ground, covered with soil and grown in the greenhouse under good growth conditions. Three weeks after sowing, the test plants were treated in the three-leaf stage.

Various dosages of the compounds according to the invention formulated as wettable powders or emulsion concentrates were sprayed onto the green parts of the plants, at an application rate of water of 600–800 l/ha (converted), and the action of the preparations were scored visually after the test plants had remained in the greenhouse for about 3–4 weeks under optimum growth conditions, comparing them to untreated control plants.

The agents according to the invention exhibit a good herbicidal activity against a broad range of economically important grass weeds and broad-leaf weeds, also in the postemergence treatment (Table 3).

3. Tolerance of crop plants

In further greenhouse experiments, seeds of a relatively large number of crop plants and weeds were placed in sandy loam ground and covered with soil.

Some of the pots were treated immediately as described under 1., those remaining were placed in the greenhouse until the plants had developed two to three true leaves and were then sprayed with various dosages of the substances according to the invention as described under 2.

Four to five weeks after application, with the plants remaining in the greenhouse, visual scoring revealed that the compounds according to the invention did not cause any damage to dicotyledon cultures, such as, for example, soya beans, cotton, oilseed rape, sugar beet and potatoes when applied both as a pre-emergence and post-emergence treatment, even at high dosages of active substance. Furthermore, crops of the Gramineae such as, for example, barley, wheat, rye, sorghum millet, maize or rice, were protected by some of the substances. Thus, the compounds of the formula I exhibit high selectivity on application for combating undesired plant growth in agricultural crops.

TABLE 2

Pre-emergence action of the compounds according to the invention

| Example No. | Dosage (kg/a.i./ha) | Herbicidal action | | | | | |
|---|---|---|---|---|---|---|---|
| | | SIA | CRS | STM | AS | ECG | LOM |
| 4 | 0,6 | 5 | 5 | 5 | 2 | 3 | 4 |
| 3 | 0,6 | 5 | 5 | 5 | 3 | 4 | 3 |
| 74 | 0,6 | 5 | 5 | 2 | 1 | 2 | 1 |
| 5 | 0,6 | 5 | 4 | 2 | 1 | 2 | 1 |
| 10 | 0,6 | 5 | 5 | 3 | 2 | 2 | 2 |
| 6 | 0,6 | 5 | 5 | 5 | 2 | 2 | 2 |

TABLE 2-continued

Pre-emergence action of the compounds according to the invention

| Example No. | Dosage (kg/a.i./ha) | Herbicidal action | | | | | |
|---|---|---|---|---|---|---|---|
| | | SIA | CRS | STM | AS | ECG | LOM |
| 138 | 0,6 | 4 | 4 | 4 | 1 | 3 | 3 |
| 139 | 0,6 | 3 | 4 | 4 | 1 | 3 | 3 |

TABLE 3

Post-emergence action of the compounds according to the invention

| Example No. | Dosage (kg/a.i./ha) | Herbicidal action | | | | | |
|---|---|---|---|---|---|---|---|
| | | SIA | CRS | STM | AS | ECG | LOM |
| 4 | 0,6 | 5 | 5 | 5 | 1 | 3 | 4 |
| 3 | 0,6 | 5 | 5 | 5 | 1 | 2 | 3 |
| 74 | 0,6 | 4 | 2 | 1 | 1 | 1 | 1 |
| 5 | 0,6 | 4 | 3 | 1 | 1 | 2 | 1 |
| 10 | 0,6 | 5 | 5 | 4 | 1 | 0 | 1 |
| 6 | 0,6 | 5 | 5 | 5 | 0 | 3 | 4 |
| 138 | 0,6 | 5 | 5 | 5 | 1 | 4 | 4 |
| 139 | 0,6 | 5 | 5 | 5 | 1 | 3 | 3 |

Abbreviations:
SIA = *Sinapis alba*
CRS = *Chrysanthemum segetum*
STM = *Stellaria media*
AS = *Avena sativa*
ECG = *Echinochloa crus-galli*
LOM = *Lolium multiflorum*
a.i. = active substance

I claim:
1. A compound of formula I

$$R_n^2 \text{—} \underset{\underset{O\text{—}SO_2\text{—}NH\text{—}\underset{\|}{C}\text{—}\underset{|}{N}\text{—}R^4}{\bigcirc}}{\overset{\overset{O}{\|}}{C}\text{—}OR^1} \qquad (I)$$

$$\phantom{R_n^2}\qquad\qquad\qquad\qquad\quad O\quad R^3$$

or a salt thereof wherein:
$R^1$ is $(C_1\text{–}C_8)$-alkyl which is monosubstituted or polysubstituted by halogen or monosubstituted or disubstituted by $(C_1\text{–}C_4)$-alkoxy, or is $(C_2\text{–}C_8)$-alkenyl or $(C_2\text{–}C_8)$-alkynyl both of which are unsubstituted, monosubstituted or polysubstituted by halogen or are monosubstituted or disubstituted by $(C_1\text{–}C_4)$-alkoxy;
$R^2$ is, independently of the other $R^2$ substituents when n>1, halogen or nitro, or is $(C_1\text{–}C_4)$-alkyl or $(C_1\text{–}C_4)$-alkoxy both of which are unsubstituted, monosubstituted or polysubstituted by halogen excluding $R^2$ is 3—$OCF_2H$;
$R^3$ is hydrogen, $(C_1\text{–}C_8)$-alkyl, $(C_2\text{–}C_8)$-alkenyl or $(C_2\text{–}C_8)$-alkynyl;
$R^4$ is a heterocyclic radical of formula $$\underset{N}{\overset{N}{\bigg\langle}}\!\!\!\!\bigcirc\!\!\!\!\overset{R^5}{\underset{R^6}{\bigg\rangle}};$$

n is 0, 1, 2 or 3;
$R^5$ and $R^6$, independently of one another, are hydrogen or halogen, or are $(C_1\text{–}C_4)$-alkyl or $(C_1\text{–}C_4)$-alkoxy both of which are unsubstituted, monosubstituted or polysubstituted by halogen or are di-$(C_1\text{–}C_4)$-alkoxy-$(C_1\text{–}C_2)$-alkyl, cyclopropyl, —$OCHR^8COOR^9$, —$NR^9R^{10}$ or $(C_1\text{–}C_4)$-alkythio;
$R^7$ is $(C_1\text{–}C_4)$-alkyl;
$R^8$ is hydrogen or $(C_1\text{–}C_4)$-alkyl; and
$R^9$ and $R^{10}$, independently of one another, are hydrogen, $(C_1\text{–}C_4)$-alkyl, $(C_2\text{–}C_4)$-alkenyl or $(C_2\text{–}C_4)$-alkynyl.

2. A compound of the formula I as claimed in claim 1 and its salts, wherein, in formula I, $R^1$ denotes $(C_1\text{–}C_4)$-alkyl which is substituted as described in claim 1, $(C_3\text{–}C_4)$-alkenyl which can be substituted as described in claim 1, or propargyl; $R^2$ denotes halogen, $(C_1\text{–}C_3)$-alkyl or $(C_1\text{–}C_3)$-alkoxy, both of which can be substituted as described in claim 1; n denotes 0, 1 or 2; $R^3$ denotes hydrogen, $(C_1\text{–}C_4)$-alkyl or allyl; $R^4$ denotes a radical of the formula $$\underset{N}{\overset{N}{\bigg\langle}}\!\!\!\!\bigcirc\!\!\!\!\overset{R^5}{\underset{R^6}{\bigg\rangle}}$$

and $R^5$ and $R^6$ independently of one another denote halogen, $(C_1\text{–}C_4)$-alkyl or $(C_1\text{–}C_4)$-alkoxy, both of which can be substituted by halogen.

3. A compound of the formula I as claimed in claim 1 and its salts, where $R^1$ denotes $(C_1\text{–}C_4)$-alkyl which is substituted as described in claim 1, $(C_3\text{–}C_4)$-alkenyl which can be substituted as described in claim 2, or propargyl; n denotes 0; $R^3$ denotes hydrogen, $R^4$ denotes a radical of the formula $$\underset{N}{\overset{N}{\bigg\langle}}\!\!\!\!\bigcirc\!\!\!\!\overset{R^5}{\underset{R^6}{\bigg\rangle}}$$

and $R^5$ and $R^6$ independently of one another denote chlorine, bromine, $(C_1\text{–}C_4)$-alkyl, $(C_1\text{–}C_4)$-alkoxy, $OCF_2H$, $OCH_2CF_3$ or $CF_3$.

4. The compound 2-chloroethyl 2-[3-(4,6-dimethoxypyrimidin-2-yl) ureidosulfonyloxy]-benzoate.

5. The compound 2-methoxyethyl 2-[3-(4,6-dimethoxypyrimidin-2-yl) ureido-sulfonyloxy]-benzoate.

6. The compound propargyl 2-[3-(4,6-dimethoxypyrimidin-2-yl) ureido-sulfonyloxy]-benzoate.

7. The compound propargyl 2-[3-(4,6-dimethoxypyrimidin-2-yl) ureido-sulfonyloxy-]-3-methoxybenzoate.

8. The compound allyl 2-[3-(4,6-dimethoxypyrimidin-2-yl)ureidosulfonyloxy]benzoate.

9. The compound 2-chloroethyl 2-[3-(4,6-dimethylpyrimidin-2-yl)ureidosulfonyloxy]benzoate.

10. The compound 2-chloroethyl 2-[3-(4-methoxy,6-methylpyrimidin-2-yl)ureidosulfonyloxy]-benzoate.

11. The compound 2-chloroethyl 2-[3-(4-methoxy, 6-chloropyrimidin-2-yl)ureidosulfonyloxy]benzoate.

12. The compound propargyl 2-[3-(4-methoxy, 6-methylpyrimidin-2-yl ureidosulfonyloxy]benzoate.

13. A herbicidal composition containing a herbicidally effective amount of a compound of formula I or salt thereof as claimed in claim 1 and a suitable inert carrier therefor.

14. A plant growth-regulating composition containing a plant growth-regulating effective amount of a compound of formula I or a salt thereof as claimed in claim 1 and a suitable inert carrier therefor.

15. A method for combatting undesired plants which comprises applying a herbicidally effective amount of a compound of formula I or salt thereof as claimed in claim 1 to a plant or an area where said plant is grown.

16. A method for regulating the growth of plants which comprises applying a plant growth-regulating effective amount of a compound of formula I or salt thereof as claimed in claim 1 to a plant or an area where said plant is grown.

* * * * *